United States Patent [19]

Coehorst

[11] 4,006,796

[45] Feb. 8, 1977

[54] EARPIECE WHICH SUBSTANTIALLY CONSISTS OF A THIN-WALLED FLEXIBLE CAPSULE FILLED WITH A LIQUID MEDIUM

[75] Inventor: Robert Francois Coehorst, Eindhoven, Netherlands

[73] Assignee: U.S. Philips Corporation, New York, N.Y.

[22] Filed: Dec. 16, 1974

[21] Appl. No.: 533,245

Related U.S. Application Data

[63] Continuation-in-part of Ser. No. 529,339, Dec. 4, 1974, abandoned.

[30] Foreign Application Priority Data

Dec. 21, 1973 Netherlands .................... 7317546
Dec. 4, 1974 Netherlands .................... 7415788

[52] U.S. Cl. .............................. 181/130; 181/135; 128/152; 179/182 R

[51] Int. Cl.$^{2}$ .................... H04R 25/02; A61B 7/02

[58] Field of Search ........... 181/135, 130; 128/151, 128/152; 179/182 R

[56] References Cited

UNITED STATES PATENTS

| | | | |
|---|---|---|---|
| 258,171 | 5/1882 | Waldstein | 181/130 |
| 2,803,247 | 8/1957 | Zwislocki | 181/135 |
| 2,934,160 | 4/1960 | Touson | 181/130 |
| 3,131,241 | 4/1964 | Mendelson | 181/135 |
| 3,736,929 | 6/1973 | Mills | 128/152 |
| 3,783,864 | 1/1974 | Moller | 128/152 |

*Primary Examiner*—Stephen J. Tomsky
*Attorney, Agent, or Firm*—Frank R. Trifari; Bernard Franzblau

[57] ABSTRACT

An earpiece which takes the form of a pouch made of a plastics foil which surrounds a less pliant plastics tube in an airtight manner and is filled with a sluggishly moving jelly-like paste.

A not readily movable compression ring provided with a funnel shaped portion which is clear of the tube ensures that the pouch is filled in such a way that during use the pouch perfectly engages with the inner wall of the auditory canal.

17 Claims, 6 Drawing Figures

EARPIECE WHICH SUBSTANTIALLY CONSISTS OF A THIN-WALLED FLEXIBLE CAPSULE FILLED WITH A LIQUID MEDIUM

This application is a continuation-in-part of application Ser. No. 529,339, filed Dec. 4, 1974, and now abandoned.

The invention relates to an earpiece which substantially consists of a thin-walled flexible capsule filled with a liquid medium and which in the longitudinal direction has an acoustic duct which is to be acoustically coupled to a hearing aid via a flexible plastic tube.

Such an earpiece is known from U.S. Pat. No. 2,934,160. The wall of the oblong capsule of said earpiece is made of a synthetic material. The capsule is filled with a liquid such as oil or water. A drawback of said capsule is that it is substantially not capable of deformation so that insertion of the earpiece into the inner auditory canal is irritating to the wearer.

The invention is an attempt to mitigate said drawback and is characterized in that the capsule consists made of a holder of a plastic foil, which is disposed around and at one end of a plastic tube which is not very flexible, the holder being filled with a jelly-like paste.

By making the capsule wall of a foil and owing to the more sluggish deformation of the paste in comparison with oil or water, the contact with the inner wall of the audiotory canal becomes definitely more pleasant to the wearer.

An earpiece according to the invention is characterized in that at the side thereof to be connected to the hearing aid, the plastic tube is provided with a compression ring with a conical compression face which co-operates with the holder.

The compression ring is slipped along the tube, the conical compression face compressing the contents of the pouch. Said pouch then very precisely assumes the shape of the interior of the auditory canal. Thus, complete acoustic sealing of said canal is achieved.

In an embodiment of the invention the holder takes the form of a pouch and at the said other side it is provided with a hole in which the plastic tube is fitted and is connected thereto in an air-tight manner. The connection is made with a cement.

A modification of said embodiment has a holder which, at the side adapted for connection to the hearing aid, is connected to the plastic tube in an air-tight manner and the compression face co-operating therewith takes the form of a funnel which does not make contact with the plastic tube.

A different embodiment of the invention is characterized in that the holder takes the form of a tubular pouch, which is slipped over the plastic tube. A part of the inner wall of the tubular pouch is attached to the front end of the plastic tube.

In a modification thereof both the inner and the outer wall of the tubular holder is attached to a flange-shaped ring at the side for connection of the hearing aid, and the compression face has a tapered cross-section, which face can be clamped in the ring.

In order to retain the compression ring, the diameter of the hole of the compression ring is slightly smaller than the outer diameter of the tube. Said ring then fits tightly around the tube.

To remove the earpiece from the auditory canal, the compression ring must be slipped away first so that the pressure exerted on the contents of the pouch decreases and said pouch comes clear of the interior of the auditory canal, thus permitting the earpiece to be readily removed from the auditory canal without irritation. Slipping away the compression ring and removal of the earpiece from the auditory canal is effected in one movement. In order to accomplish this the compression ring may be provided either with a flange or a pull-pin.

An embodiment which performs highly satisfactorily is characterized in that the end of the plastic tube is provided with a rigid retaining ring, which at the circumference is in airtight connection with the edge of the pouch.

In order to provide adequate "ventilation" of the interior ear space to the inside of the earpiece, an embodiment of the invention is characterized in that a part of the tube behind the capsule is provided with a movable ventilation ring disposed over a ventilation opening provided in the tube. The compression ring may then also serve as a ventilation ring.

The invention will be described in more detail with reference to the accompanying drawing in which.

Figure 1:
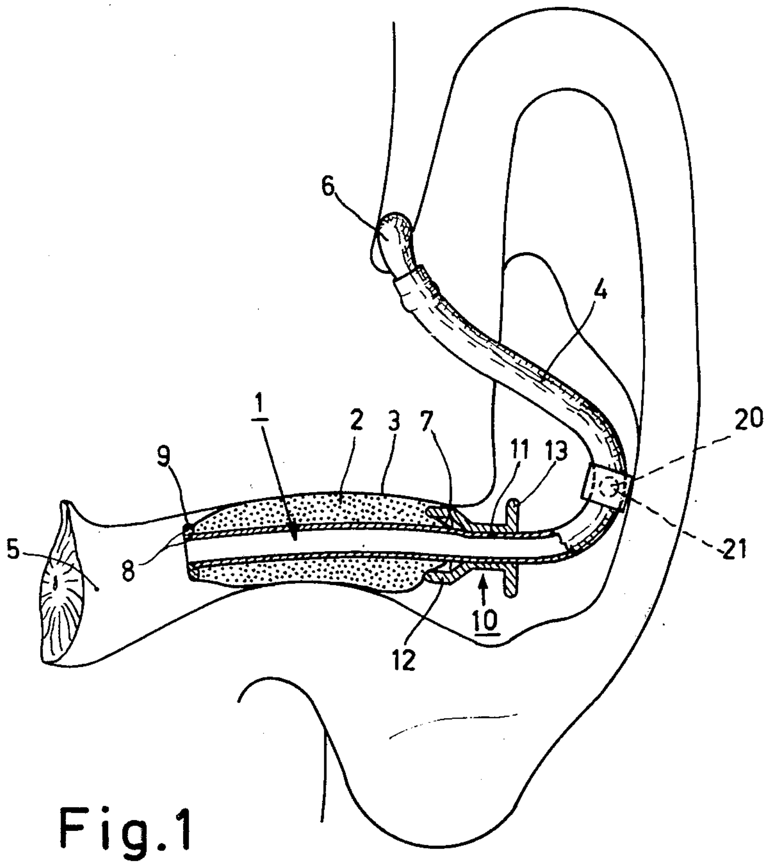
FIG. 1 is a longitudinal section of an earpiece according to the invention inserted in an ear.
Figure 2:
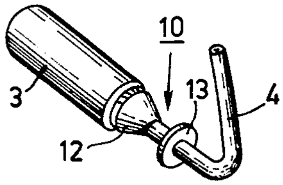
FIG. 2 is a perspective view of said earpiece.
Figure 3:
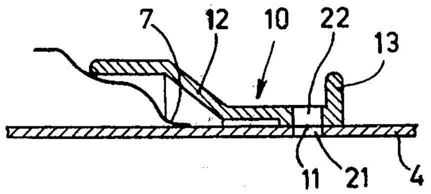
FIG. 3 is a cross-section of the compression ring used in conjunction therewith.

In FIGS. 1 through 3 the earpiece 1 consists of a capsule 2 which essentially consists of a pouch 3 made of a very thin foil, for example silicone rubber with a thickness of 100–200$\mu$um. Said pouch is disposed around the end of a flexible but relatively stiff plastic tube 4. Said tube serves as an acoustic duct and constitutes the connection between the inner auditory canal 5 and the hearing aid 6 which is disposed behind the ear.

The pouch of the capsule 2 is filled with a jelly-like paste and is fixed to the tube 4 in an airtight manner, i.e. directly to the tube at the location 7 and via a rigid retaining ring 9 at the end 8 of the tube.

Around the tube 4 a compression ring 10 is disposed. Said ring is movable along the tube 4.

The compression ring 10 has a conical or funnel-shaped portion 12 which engages with the pouch of capsule 3 at the location of connection 7. The ring is not readily movable because the inner diameter 11 of the compression ring 10 is slightly smaller than the outer diameter of the tube 4. Thus, the compression ring 10 fits tightly around tube 4.

Figure 4:
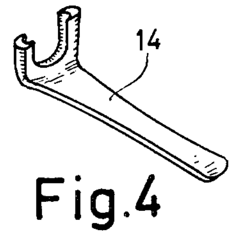
FIG. 4 is an extraction tool.
Figure 5:
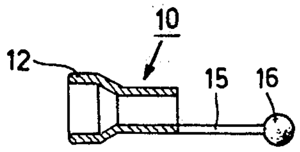
FIG. 5 is a modification of the compression ring according to the invention.

Compression ring 10 is furthermore provided with a flange 13 which allows the compression ring to be moved. By means of an aid 14, as shown in FIG. 4, ring 10 can be moved clear of the capsule so that the pressure on the pouch is relieved and the capsule then may readily be taken out of the ear.

It is alternatively possible to provide the compression ring 10 with a pull-pin 15 and a knob 16 instead of with a flange 13.

The operaton is as follows.

The earpiece 1 is slipped into the auditory canal of the ear. The compression ring 10 is then disposed far enough from the capsule so that the pouch — and thus the capsule — loosely surrounds the tube 4. Insertion of the earpiece thus does not cause any irritation of the very sensitive inner wall of the auditory canal.

When the capsule is correctly positioned, the compression ring is slid in the direction of the capsule. The funnel-shaped portion 12 compresses the pouch and forces the contents of the pouch, i.e. the jelly-like paste, forwards. The auditory canal is thereby fully sealed without giving rise to any irritation. The foil material of the pouch perfectly adapts itself to the shape of the auditory canal. The jelly-like paste ensures that this does not happen too quickly. As a result the auditory canal around the acoustic duct is completely sealed.

The tight fit ensures that the compression ring remains on the tube in the desired position.

To enable ventilation of the interior of the auditory canal 5 in front of the capsule 1, a movable, closed ventilation ring 20 is disposed behind the capsule 1, which ring can cover the vent hole 21 in tube 4. FIG. 3 shows that compression ring 10 may also perform the function of a ventilation ring and is therefore provided with a hole 22, which in the drawn position is disposed above vent hole 21. A slight rotation of compression ring 10 closes vent hole 21.

Figure 6:
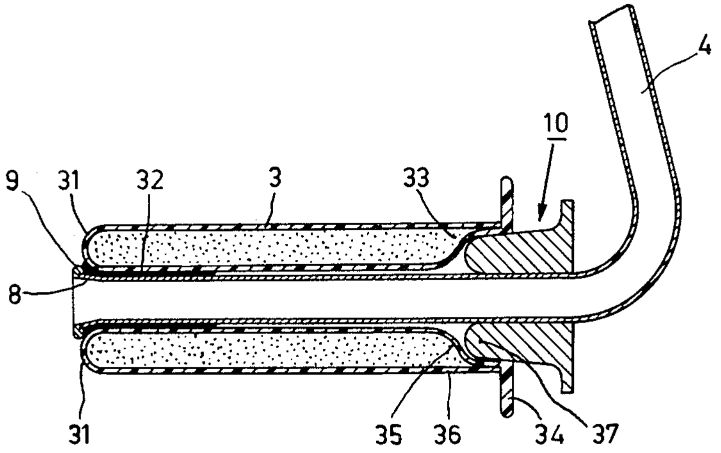
FIG. 6 is a longitudinal section of a different earpiece according to the invention.

FIG. 6 shows a modification according to the invention. The holder 3 takes the form of a tubular pouch and is slipped over the end 8 of the plastic tube 4. The closed end 31 is cemented to said end 8 over a part 32 (approximately ⅓ of the total length of the holder). The other end 33 loosely surrounds the plastics tube 4 and terminates in a flange-shaped ring 34, to which the edges 35 and 36 are connected in an air-tight manner. The compression ring 10 is provided with a tapered part 37 whose diameter continuously increases in the direction of the holder 3 and which can be slid into ring 34 and can be clamped therein. The paste in the holder 2 is then compressed.

What is claimed is:

1. An earpiece comprising, an oblong thin-walled flexible container made of a plastic foil filled with a jelly-like paste material and having an acoustic duct extending therethrough in the longitudinal direction, and a flexible plastic tube which is less pliant than the plastic foil container and is located in the acoustic duct and is adapted for acoustically coupling the duct to a hearing aid, said container being disposed around and at one end of the plastic tube.

2. An earpiece as claimed in claim 1 further comprising a compression ring coupled to the plastic tube and located at that side of the container intended to be coupled to the hearing aid, said compression ring having a conical compression face which cooperates with the container to deform same.

3. An earpiece as claimed in claim 2 wherein the container comprises a pouch provided with a hole in which hole the plastic tube is fitted and is connected thereto in an air-tight manner.

4. An earpiece as claimed in claim 2 wherein the container, at the side adapted to be coupled to the hearing aid, is connected to the plastic tube in an air-tight manner and that the compression face which cooperates therewith takes the form of a funnel which surrounds and is spaced apart from the plastic tube.

5. An earpiece as claimed in claim 2 wherein the diameter of the hole of the compression ring is slightly smaller than the outer diameter of the plastic tube.

6. An earpiece as claimed in claim 2 wherein the compression ring is provided with a flange.

7. An earpiece as claimed in claim 2 wherein the compression ring is provided with a pull-pin.

8. An earpiece as claimed in claim 2 wherein part of the tube behind the capsule is provided with a movable ventilation ring which is disposed over a ventilation hole provided in the tube.

9. An earpiece as claimed in claim 2 wherein the compression ring has a hole therein adapted to mate with a hole in the plastic tube whereby the compression ring also functions as a ventilation ring.

10. An earpiece as claimed in claim 2 wherein the end of the plastic tube remote from the hearing aid includes a rigid retaining ring connected at its periphery to the container in an air-tight manner.

11. An earpiece as claimed in claim 1 wherein the container comprises a tubular pouch disposed about the plastic tube and which, at the side remote from the hearing aid, has a part of its inner wall attached to the plastic tube.

12. An earpiece as claimed in claim 11, wherein both the inner and the outer wall of the tubular pouch is attached to a flange-shaped ring located at the side of the pouch adapted to be coupled to the hearing aid, and further comprising a compression ring having a compression face of tapered cross-section adapted to be clamped in the ring.

13. An earpiece as claimed in claim 1 wherein the end of the plastic tube is provided with a rigid retaining ring connected to the container at its circumference.

14. An earpiece as claimed in claim 1 wherein the container comprises a pouch with a hole at the end thereof, the plastic tube being disposed within said hole and connected to the pouch in an air-tight manner.

15. An earpiece comprising, an oblong thin-walled flexible container made of a plastic foil and having a single cavity filled with a slow moving jelly-like paste material, said container including an acoustic duct extending therethrough in the longitudinal direction, a rigid flexible plastic tube disposed within the acoustic duct and adapted for acoustically coupling the duct to a hearing aid, said flexible container being dimensioned to slip easily into the auditory canal of the user of the earpiece and being connected to the plastic tube in an airtight manner.

16. An earpiece as claimed in claim 15 further comprising a compression ring movably mounted to the plastic tube at the side of the container intended to be coupled to the hearing aid, said compression ring having a tubular portion coaxially surrounding the plastic tube and a conical compression portion adapted to engage said container to compress same and cause the jelly-like paste to deform the container so that it adapts itself to the shape of the auditory canal of the user of the earpiece.

17. A hearing apparatus comprising the earpiece as claimed in claim 15 and further comprising a hearing aid coupled to the end of the plastic tube remote from that end of the tube disposed within the container duct.

* * * * *

UNITED STATES PATENT AND TRADEMARK OFFICE
CERTIFICATE OF CORRECTION

PATENT NO. : 4,006,796
DATED : February 8, 1977
INVENTOR(S) : ROBERT FRANCOIS COEHORST It is certified that error appears in the above-identified patent and that said Letters Patent are hereby corrected as shown below:

IN THE SPECIFICATION

Column 1, line 23, "made of a holder" should be

--of a holder made--;

line 55, after "pouch" cancel "," (comma);

Column 2, line 31, after "invention" insert -- and--.

IN THE CLAIMS

Claim 8, line 1, before "part" insert --a--.

Signed and Sealed this

Fourteenth Day of June 1977

[SEAL]

*Attest:*

RUTH C. MASON
*Attesting Officer*

C. MARSHALL DANN
*Commissioner of Patents and Trademarks*